US008842895B2

(12) United States Patent  (10) Patent No.: US 8,842,895 B2
Sugiura  (45) Date of Patent: Sep. 23, 2014

(54) MAGNETIC RESONANCE IMAGING APPARATUS AND SCANNING-CONDITION SETTING METHOD (75) Inventor: Satoshi Sugiura, Tochigi-Ken (JP)

(73) Assignees: Toshiba Medical Systems Corporation, Tochigi (JP); Kabushiki Kaisha Toshiba, Tokyo (JP)

(*) Notice: Subject to any disclaimer, the term of this patent is extended or adjusted under 35 U.S.C. 154(b) by 539 days.

(21) Appl. No.: 12/413,520

(22) Filed: Mar. 28, 2009

(65) Prior Publication Data
US 2009/0245607 A1 Oct. 1, 2009

(30) Foreign Application Priority Data
Mar. 31, 2008 (JP) .................. 2008-093233

(51) Int. Cl.
G06K 9/00 (2006.01)

(52) U.S. Cl.
USPC .......................................... 382/131

(58) Field of Classification Search
USPC ............... 382/131; 378/4–20, 901; 600/419; 324/307
See application file for complete search history.

(56) References Cited

U.S. PATENT DOCUMENTS

| 6,483,307 | B2 * | 11/2002 | Ookawa ................. | 324/309 |
| 7,471,757 | B2 * | 12/2008 | Tsukagoshi et al. ............ | 378/4 |
| 2008/0049889 | A1 | 2/2008 | Tsukagoshi et al. | |
| 2008/0071166 | A1 * | 3/2008 | Miyazaki .............. | 600/419 |
| 2008/0265884 | A1 | 10/2008 | Miyazaki | |

FOREIGN PATENT DOCUMENTS

| CN | 101132666 A | 2/2008 | |
| CN | 101138497 A | 3/2008 | |
| JP | 06261884 A * | 9/1994 | ............ A61B 5/055 |
| JP | 2003190119 A | 7/2003 | |
| JP | 2003-290171 A | 10/2003 | |
| JP | 2004-201779 A | 7/2004 | |
| JP | 2005-278919 A | 10/2005 | |
| JP | 2006-167208 A | 6/2006 | |
| JP | 2006-255189 A | 9/2006 | |
| JP | 2006320527 A | 11/2006 | |
| JP | 5361236 B2 | 10/2009 | |
| WO | 2004080301 A1 | 9/2004 | |
| WO | 2008096677 A1 | 8/2008 | |

OTHER PUBLICATIONS

Ding et al. ("Improved Coverage in Dynamic Contrast-Enhanced Cardiac MRI Using Interleaved Gradient-Echo EPI" NMR in Biomedicine vol. 7, Issue 1-2, pp. 83-88, Mar. 1994).*
Song et al. ("Multislice Double Inversion Pulse Sequence for Efficient Black-Blood MRI" Magnetic Resonance in Medicine 47:616-620 (2002)).*

(Continued)

Primary Examiner — Marcos D. Pizarro
Assistant Examiner — Sue Tang
(74) Attorney, Agent, or Firm — Yoshida & Associates, LLC (57) ABSTRACT According to a Magnetic Resonance Imaging (MRI) apparatus, a scanning-parameter limit calculating unit creates examination information that represents scanning conditions for collection of magnetic resonance signal data based on scanning parameters set by an operator; a scanning-condition edit/scan positioning unit creates a time chart that indicates the type and a sequential execution order of an event to be executed when collecting magnetic resonance signal data based on the examination information created by the scanning-parameter limit calculating unit, and causes a time-chart display unit to display the created time chart.

20 Claims, 10 Drawing Sheets (56) References Cited

OTHER PUBLICATIONS

CN Office Action with English Summary for CN Application No. 200910132915.7 mailed on Aug. 19, 2010 (7 pages).

JP Office Action with English Translation for JP Application No. 2008-093233 mailed on Jan. 8, 2013.

Japanese Office Action with its English translation for Japanese Patent Application No. 2013-048296 mailed on May 20, 2014.

* cited by examiner

| PROCESSING | SETTING | PLAN SELECTION | HIGHLIGHT | TE 2.0 | SNR: 100.0% | BANDWIDTH: 488 |

SAR: ----- | TOTAL SCANNING TIME: 20 | SCANNING TIME: 20 | NUMBER OF SCANS: 1 | MAXIMUM NUMBER OF SLICES: 128 | RESOLUTION: 3.1×1.4 mm

IMAGING: FFE3D2_125k

TR: 5.0 ▶ 5.4 ◀ 8.5  MIN ☐

NUMBER OF SLICES: 10 ▶ 10 ◀ 40 (5)  MAX ☐

SLICE THICKNESS: 10.00 ▶ 10.00 ◀ 10.00 (128)

NUMBER OF TIMES OF SUMMATION: 1.0 ▶ 1.0 ◀ 64.0

PE-MATRIX: 32 ▶ 96 ◀ 208 (256) ☐

PE-FOV: 22.9 ▶ 30.0 ◀ 50.0 (36.0) ☐

ALIASING PREVENTION: NONE

FLIP ANGLE: 1 ▶ 10 ◀ 20

FLOP ANGLE: ▷ ☐

IR PULSE: ON ☐
TI: 166 ▶ 220 ◀ 640 ☐

FAT SUPPRESSION PULSE: OFF ☐

GATING MODE: ECG ☐

DYNAMIC: OFF ☐

[REGISTER AND GO TO NEXT] [REGISTER AND END] [RESET] [OTHER PARAMETERS] [CANCEL]

MAGNETIC RESONANCE IMAGING APPARATUS AND SCANNING-CONDITION SETTING METHOD

CROSS-REFERENCE TO RELATED APPLICATIONS

This application is based upon and claims the benefit of priority from the prior Japanese Patent Application No. 2008-93233, filed on Mar. 31, 2008; the entire contents of which are incorporated herein by reference.

BACKGROUND OF THE INVENTION

1. Field of the Invention

The present invention relates to a magnetic resonance imaging apparatus that takes an image of a subject by collecting data about the inside of the subject by using magnetic resonance phenomenon, and a scanning-condition setting method.

2. Description of the Related Art

Conventionally, a magnetic resonance imaging apparatus is an apparatus that images an arbitrary cross section of a subject, such as a human body, by using various contrasts between tissues. Such magnetic resonance imaging apparatus performs imaging by executing a procedure so-called a pulse sequence, which sequentially defines events representing timing of application of a radio-frequency pulse or a gradient magnetic field pulse, and timing of data collection.

An operator of the magnetic resonance imaging apparatus appropriately sets various scanning parameters prior to a scan, and obtains information required for an examination, such as contrast, Signal to Noise ratio (SN ratio), spatial resolution, flow velocity, and diffusion. The scanning parameters include, for example, a Repetition Time (TR), Echo Time (TE), the number of matrices, Field of View (FOV), the number of slices, and slice thickness.

Figure 11:
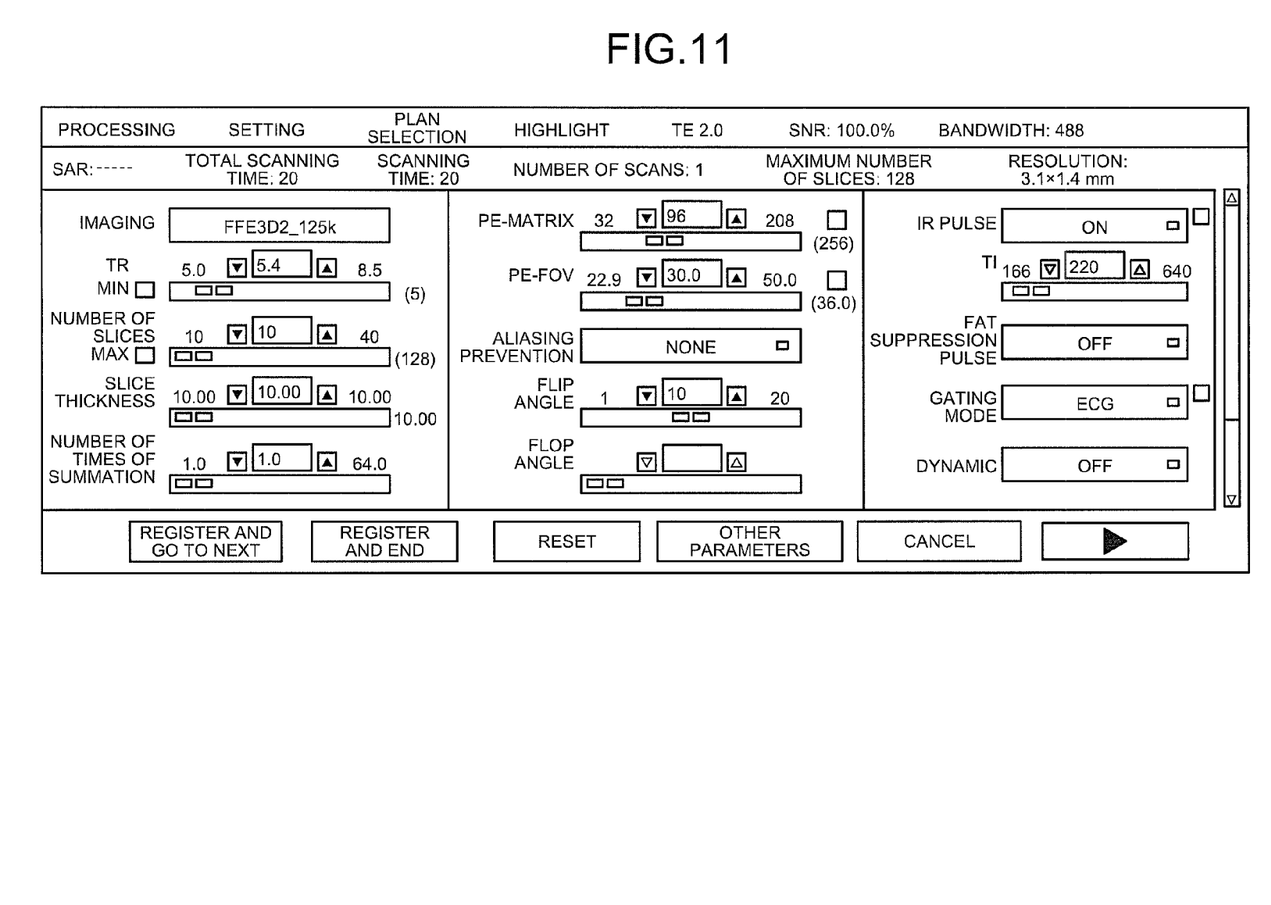
FIG. 11 is a schematic diagram of an example of a user interface for editing scanning parameters according to a conventional magnetic resonance imaging apparatus.

FIG. 11 is a schematic diagram that depicts an example of a user interface for editing scanning parameters according to a conventional magnetic resonance imaging apparatus. FIG. 11 depicts a scanning-condition edit screen including various scanning parameters as edit items. The operator sets a value of a required scanning parameter by inputting a numerical value or operating a user interface, such as a slider or a button, on the scanning-condition edit screen shown in FIG. 11.

Additionally to the scanning parameters described above, the operator edits scanning conditions, such as an imaging method (type of pulse sequence, for example, spin echo, or Echo Planar Imaging (EPI)), the type of a prepulse, such as a fat suppression pulse or an inversion pulse, the number of prepulses, the order of prepulses, and the order of slice excitation, in accordance with a purpose. As a technology for confirming spatial arrangement of such prepulses and scanning pulses, there is a technology of displaying a slice region on a positioning image (for example, see JP-A 2003-290171 (KOKAI)). A positioning image used in the technology is called a graphic locator, for example.

However, according to the conventional technology described above, the operator can confirm spatial arrangement of a prepulse or a scanning pulse, but cannot confirm temporal order of the prepulses or the scanning pulses. In other words, according to the conventional technology, when changing a scanning condition, the operator cannot obtain information that influences an image to be obtained, for example, timing of collection of data at a target scan position, the type of each prepulse to be applied, the order and the frequency of application of prepulses.

SUMMARY OF THE INVENTION

According to one aspect of the present invention, a magnetic resonance imaging apparatus includes a scanning-condition creating unit that creates examination information that represents a scanning condition for collection of data indicating an inside of a subject, based on a value of a scanning parameter set by an operator; a chart display-control unit that creates and causes a display unit to display a time chart that indicates a type and a sequential execution order of an event to be executed when performing the collection of data, based on the examination information created by the scanning-condition creating unit; a data collecting unit that collects data indicating the inside of the subject by using the examination information created by the scanning-condition creating unit; and an image reconstructing unit that reconstructs an image from the data collected by the data collecting unit.

According to another aspect of the present invention, a scanning-condition setting method of a magnetic resonance imaging apparatus, includes creating examination information that represents a scanning condition for collection of data indicating an inside of a subject based on a value of a scanning parameter set by an operator; and creating and causing a display unit to display a time chart indicating a type and a sequential execution order of an event to be executed when performing the collection of data, based on the created examination information.

DETAILED DESCRIPTION OF THE INVENTION

Exemplary embodiments of a magnetic resonance imaging apparatus and a scanning-condition setting method according to the present invention will be explained below in detail with reference to the accompanying drawings. A Magnetic Resonance Imaging apparatus is referred to as an MRI apparatus in the following embodiments.

Figure 1:
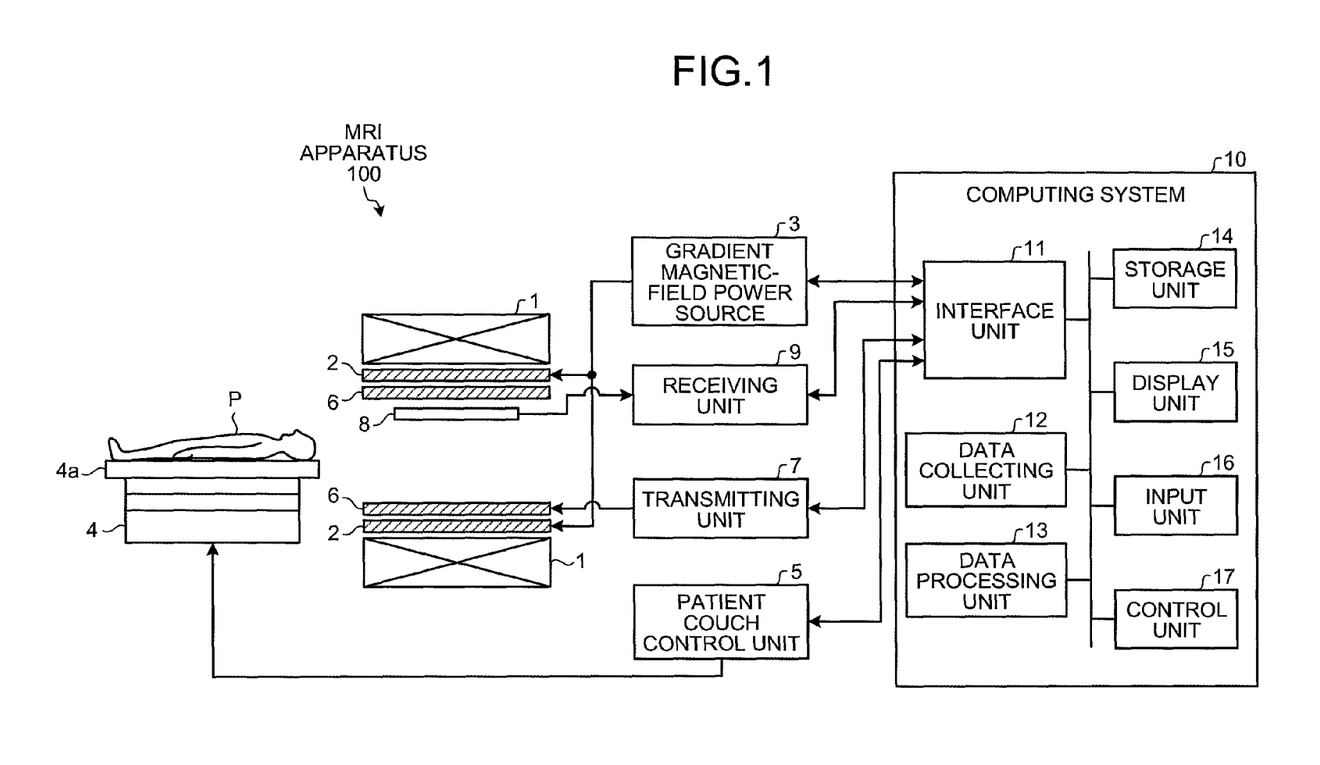
FIG. 1 is a schematic diagram of a general configuration of an MRI apparatus according to an embodiment of the present invention.

First of all, a general configuration of an MRI apparatus according to an embodiment of the present invention is explained below with reference to FIG. 1. FIG. 1 is a schematic diagram of a general configuration of an MRI apparatus 100 according to the embodiment. As shown in FIG. 1, the MRI apparatus 100 includes a static magnetic-field magnet 1, a gradient magnetic-field coil 2, a gradient magnetic-field power source 3, a patient couch 4, a patient couch control unit 5, a Radio Frequency (RF) transmitting coil 6, a transmitting unit 7, a RF receiving coil 8, a receiving unit 9, and a computing system 10.

The static magnetic-field magnet 1 is formed in a hollow cylindrical shape, and generates a uniform static magnetic field in a space its inside. For example, a permanent magnet, or a super conducting magnet is used as the static magnetic-field magnet 1.

The gradient magnetic-field coil 2 is formed in a hollow cylindrical shape, and is arranged inside the static magnetic-field magnet 1. The gradient magnetic-field coil 2 is formed of three coils in combination corresponding to x, y, and z axes orthogonal to one another. The three coils generate gradient magnetic fields along three directions of the x, y, and z axes, respectively, by individually receiving a current supply from the gradient magnetic-field power source 3. It is assumed that the z axis direction is the same direction as the static magnetic field.

The gradient magnetic fields of the x, y, and z axes generated by the gradient magnetic-field coil 2 correspond to, for example, a slice-selective gradient magnetic field Gs, a phase encoding gradient magnetic field Ge, and a readout gradient magnetic field Gr, respectively. The slice-selective gradient magnetic field Gs is used for arbitrarily setting a scan cross section. The phase encoding gradient magnetic field Ge is used for changing a phase of a magnetic resonance signal in accordance with a spatial position. The readout gradient magnetic field Gr is used for changing the frequency of a magnetic resonance signal in accordance with a spatial position.

The gradient magnetic-field power source 3 supplies a current to the gradient magnetic-field coil 2 based on pulse-sequence execution data sent from the computing system 10.

The patient couch 4 includes a top plate 4a on which a subject P is to be placed. Under the control of the patient couch control unit 5, the patient couch 4 inserts the top plate 4a on which the subject P is placed, into a hole (a scanning space) of the gradient magnetic-field coil 2. Usually, the patient couch 4 is placed such that the longitudinal direction of the patient couch 4 is to be parallel to the central axis of the static magnetic-field magnet 1.

The patient couch control unit 5 controls the patient couch 4. The patient couch control unit 5 moves the top plate 4a in the longitudinal direction and upward and downward directions by driving the patient couch 4.

The RF transmitting coil 6 is arranged inside the gradient magnetic-field coil 2, and generates an RF magnetic field by receiving supply of a radio-frequency pulse from the transmitting unit 7.

The transmitting unit 7 sends a radio-frequency pulse corresponding to a Larmor frequency to the RF transmitting coil 6 based on pulse-sequence execution data sent from the computing system 10. Specifically, the transmitting unit 7 includes an oscillating unit, a phase selecting unit, a frequency converting unit, an amplitude modulating unit, and a radio-frequency power amplifying unit. The oscillating unit generates a radio-frequency signal of a resonance frequency unique to a subject nucleus in the static magnetic field. The phase selecting unit selects a phase of the radio-frequency signal. The frequency converting unit converts a frequency of the radio-frequency signal output by the phase selecting unit. The amplitude modulating unit modulates amplitude of the radio-frequency signal output by the frequency converting unit in accordance with, for example, a sinc function. The radio-frequency power amplifying unit amplifies the radio-frequency signal output by the amplitude modulating unit. As a result of operation performed by the above units, the transmitting unit 7 transmits a radio-frequency pulse corresponding to a Larmor frequency to the RF transmitting coil 6.

The RF receiving coil 8 is arranged inside the gradient magnetic-field coil 2, and receives a magnetic resonance signal irradiated from the subject owing to an influence of the RF magnetic field. Upon receiving a magnetic resonance signal, the RF receiving coil 8 outputs the magnetic resonance signal to the receiving unit 9.

The receiving unit 9 creates magnetic-resonance signal data based on the magnetic resonance signal output by the RF receiving coil 8 based on pulse-sequence execution data sent from the computing system 10. Upon creating magnetic-resonance signal data, the receiving unit 9 sends the magnetic-resonance signal data to the computing system 10.

The computing system 10 performs total control of the MRI apparatus 100, data collection, image reconstruction, and the like. Specifically, the computing system 10 includes an interface unit 11, a data collecting unit 12, a data processing unit 13, a storage unit 14, a display unit 15, an input unit 16, and a control unit 17.

The interface unit 11 is connected to the gradient magnetic-field power source 3, the patient couch control unit 5, the transmitting unit 7, and the receiving unit 9; and controls input and output of signals that are transmitted or received between each of the connected units and the computing system 10.

The data collecting unit 12 collects magnetic-resonance signal data sent from the receiving unit 9 via the interface unit 11. Upon collecting magnetic-resonance signal data, the data collecting unit 12 stores the collected magnetic-resonance signal data into the storage unit 14.

The data processing unit 13 performs post-processing, i.e., reconstruction processing, such as a Fourier transform, on the magnetic-resonance signal data stored in the storage unit 14, and creates spectrum data or image data of a desired nuclear spin inside the subject P.

The storage unit 14 stores therein magnetic-resonance signal data collected by the data collecting unit 12, and image data created by the data processing unit 13, with respect to each of the subject P.

The display unit 15 displays thereon various information, such as spectrum data or image data, under the control of the control unit 17. A display device, such as a liquid crystal display, can be used as the display unit 15.

The input unit 16 receives various instructions and information input from an operator. As the input unit 16, input devices, for example, pointing devices, such as a mouse or a trackball, a selecting device, such as a mode switch, and a keyboard, can be used as required.

The control unit 17 includes a Central Processing Unit (CPU) and a memory, both of which are not shown, and totally controls the MRI apparatus 100.

As described above, a general configuration of the MRI apparatus 100 according to the embodiment has been explained. According to the MRI apparatus 100 of the embodiment configured in this way, the computing system 10 causes the display unit 15 to display a time chart that indicates timing with which a target scan position is collected, what kind of prepulse to be applied, and in what order and how frequently each prepulse is to be applied, thereby allowing an operator to confirm easily influence on an image due to a change in scanning parameters.

Figure 2:
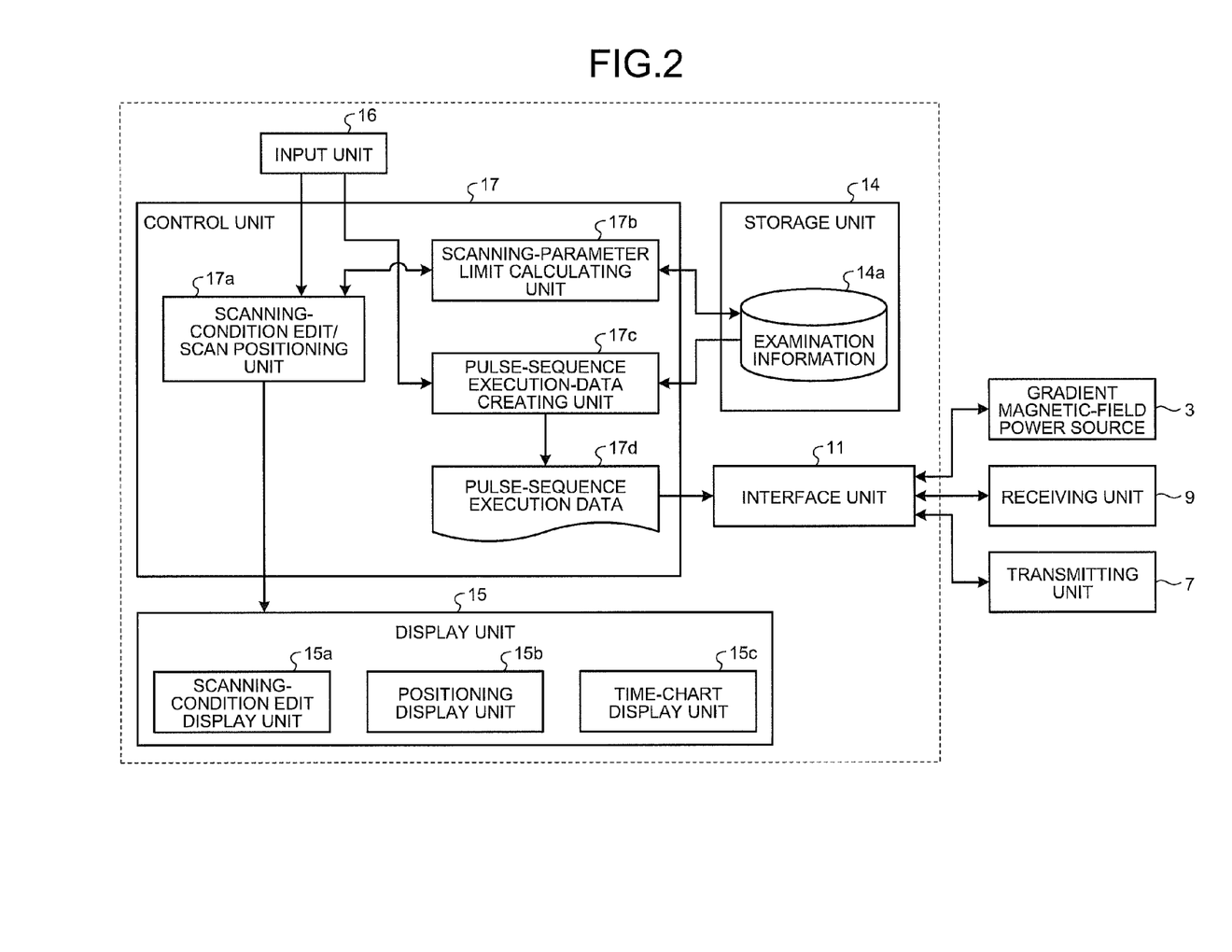
FIG. 2 is a functional block diagram of a detailed configuration of a computing system according to the embodiment.

Functions that the computing system 10 has are specifically explained below. At first, a detailed configuration of the computing system 10 according to the embodiment is explained below in detail with reference to FIG. 2. FIG. 2 is a functional block diagram that depicts a detailed configuration of the computing system 10 according to the embodiment. FIG. 2 depicts a detailed configuration of the display unit 15, the control unit 17, and the storage unit 14, and interrelations among the interface unit 11, the storage unit 14, the display unit 15, the input unit 16, and the control unit 17.

As shown in FIG. 2, the storage unit 14 stores therein particularly examination information 14a. The examination information 14a indicates scanning conditions in accordance with the type of a scan among various scans, and includes values of various scanning parameters included in the scanning conditions, such as the type of a scan, the position of a slice, a slice thickness, the number of slices, and the like.

As shown in FIG. 2, the display unit 15 includes particularly a scanning-condition edit display unit 15a, a positioning display unit 15b, and a time-chart display unit 15c.

The scanning-condition edit display unit 15a displays information about scanning conditions. Specifically, under the control of a scanning-condition edit/scan positioning unit 17a, the scanning-condition edit display unit 15a displays an area for inputting and outputting information about a scanning condition with respect to each of the scanning parameters, and a scanning-condition edit screen that includes a user interface for receiving various operations from the operator.

The positioning display unit 15b displays a positioning image to be a reference when determining the position of a slice to be scanned. Moreover, the positioning display unit 15b displays a figure indicating a slice region on the positioning image based on scanning conditions set by the operator. When a scanning condition is changed by the operator, the positioning display unit 15b changes the position and/or the shape of a figure indicating a slice region in a synchronized manner with display of the scanning conditions performed by the scanning-condition edit display unit 15a.

The time-chart display unit 15c displays a time chart created by the scanning-condition edit/scan positioning unit 17a.

As shown in FIG. 2, the control unit 17 includes particularly the scanning-condition edit/scan positioning unit 17a, a scanning-parameter limit calculating unit 17b, and a pulse-sequence execution-data creating unit 17c.

The scanning-condition edit/scan positioning unit 17a receives information about edit of a scanning condition and positioning of a slice. Moreover, the scanning-condition edit/scan positioning unit 17a creates a time chart that indicates types and order of events to be executed when collecting magnetic-resonance signal data based on the examination information 14a created by the scanning-parameter limit calculating unit 17b, and causes the time-chart display unit 15c to display the created time chart.

Specifically, to begin with, when receiving a display request for a scanning-condition edit screen 20 from the operator via the input unit 16, the scanning-condition edit/scan positioning unit 17a controls and causes the scanning-condition edit display unit 15a to display the scanning-condition edit screen 20.

Moreover, when receiving an operation of setting a value for a scanning parameter on the scanning-condition edit screen 20 from the operator via the input unit 16, the scanning-condition edit/scan positioning unit 17a passes the set value to the scanning-parameter limit calculating unit 17b parameter by parameter of the scanning parameters. When a limit value of a scanning parameter is then returned from the scanning-parameter limit calculating unit 17b, the scanning-condition edit/scan positioning unit 17a controls and causes the scanning-condition edit display unit 15a to display the returned limit value onto the scanning-condition edit screen 20 parameter by parameter of the scanning parameters.

Moreover, when receiving a display request for a time chart from the operator via the input unit 16, the scanning-condition edit/scan positioning unit 17a reads the examination information 14a stored by the storage unit 14, and creates a time chart that indicates types and sequential execution-order of events to be executed when collecting data, based on the examination information 14a that is read.

When creating the time chart, the scanning-condition edit/scan positioning unit 17a creates a time chart 30 such that time intervals of the events to be executed are to be indicated. The scanning-condition edit/scan positioning unit 17a then controls and causes the time-chart display unit 15c to display the created time chart.

Figure 3:
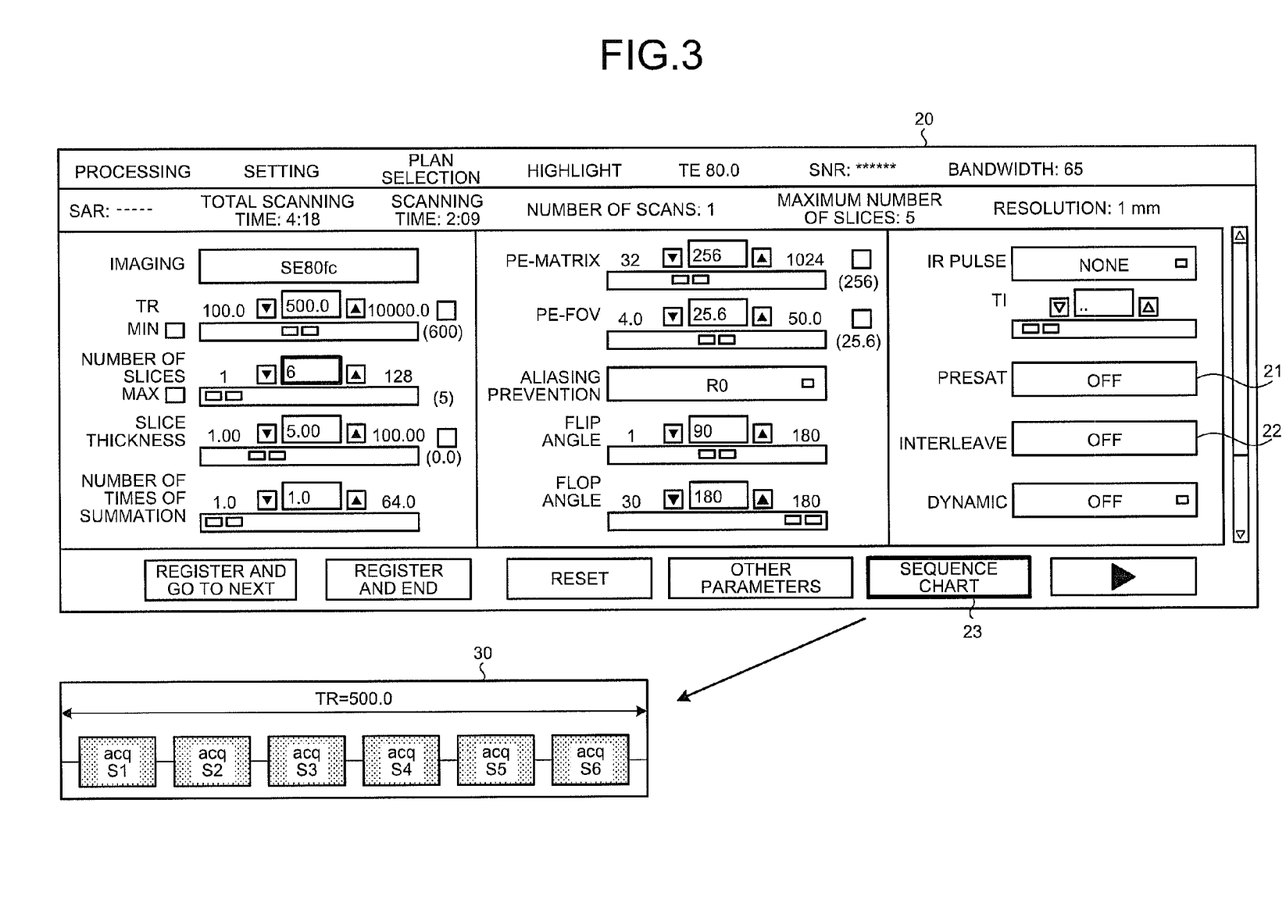
FIG. 3 is a schematic diagram for explaining display of a time chart conducted by a scanning-condition edit/scan positioning unit.

Display of a time chart conducted by the scanning-condition edit/scan positioning unit 17a is explained below in detail with reference to FIG. 3. FIG. 3 is a schematic diagram for explaining display of a time chart conducted by the scanning-condition edit/scan positioning unit 17a. FIG. 3 depicts an example of the scanning-condition edit screen 20 displayed by the scanning-condition edit display unit 15a.

As shown in FIG. 3, for example, the scanning-condition edit screen 20 includes areas for displaying values each of which is set with respect to each of the scanning parameters, such as "repetition time (TR)", "the number of slices", "slice thickness", and "the number of times of summation". According to the scanning-condition edit screen 20, the maximum number of slices that can be scanned within a set repetition time is calculated by referring to other scanning conditions and other information (for example, the weight of a patient and an RF transmission power) stored by the storage unit 14 as the examination information 14a. An example shown in FIG. 3 depicts a case of collecting a two-dimensional spin-echo image by a multislice method, where six slices are to be collected during a repetition time TR=500 milliseconds.

Moreover, the scanning-condition edit screen 20 includes buttons for receiving various operations from the operator, for example, a presat button 21, an interleave button 22, and a sequence chart button 23 as shown in FIG. 3. The presat button 21 receives from the operator a setting request to set a presaturation pulse for suppressing signals from irrelevant portions of a scan subject. The interleave button 22 receives a reorder request to reorder a slice collection order within a repetition time. The sequence chart button 23 receives a display request for a time chart.

According to the scanning-condition edit screen 20, when the operator presses the sequence chart button 23 via the input unit 16, for example, the scanning-condition edit/scan positioning unit 17a creates and displays the time chart 30 on which figures denoting collection of data of six slices are sequentially arranged, as shown in the lower part of the FIG. 3. According to FIG. 3, "acq" denotes data collection, and "S1" to "S6" denote slice numbers from 1 to 6, respectively. The time chart 30 indicates that data collection of each slice is performed in the order of the slice numbers within the repetition time.

When the operator presses the presat button 21 on the scanning-condition edit screen 20 via the input unit 16, the scanning-condition edit/scan positioning unit 17a controls and causes the scanning-parameter limit calculating unit 17b to recalculate the number of slices, and then changes display of the scanning-condition edit screen 20 and the time chart 30 based on a calculation result.

Specifically, when the operator presses the presaet button 21 on the scanning-condition edit screen 20, the scanning-condition edit/scan positioning unit 17a controls and causes the scanning-parameter limit calculating unit 17b to recalculate the number of slices that can be scanned within a repetition time when a presaturation pulse is added immediately before data collection of each slice, and causes the scanning-condition edit screen 20 to display the recalculated number of slices.

Figure 4:
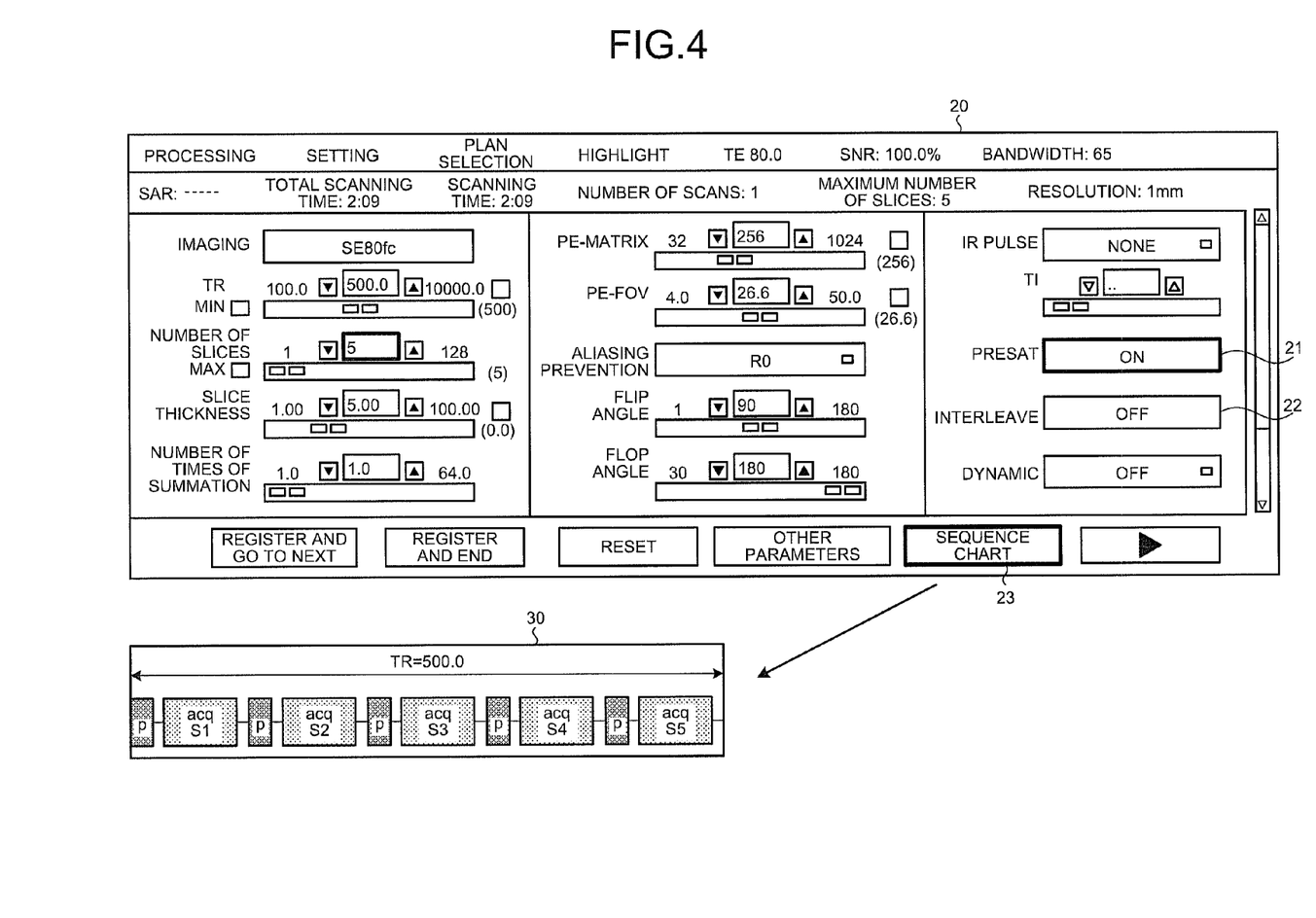
FIG. 4 is a schematic diagram for explaining display of the time chart when a presat button is pressed.

FIG. 4 is a schematic diagram for explaining display of the time chart 30 when the presat button 21 is pressed. When the presat button 21 is pressed, the scanning-condition edit/scan positioning unit 17a changes display of the number of slices, for example, as shown in FIG. 4, from six to five.

Moreover, the scanning-condition edit/scan positioning unit 17a changes display of the time chart 30 displayed by the time-chart display unit 15c based on the number of slices recalculated by the scanning-parameter limit calculating unit 17b.

For example, the scanning-condition edit/scan positioning unit 17a changes the number of figures denoting data collection indicated on the time chart 30 to five from six as shown in the lower part of FIG. 4, and adds a figure "p" denoting a presaturation pulse immediately before each of "S1" to "S5" denoting data collection.

In this way, as the scanning-condition edit/scan positioning unit 17a changes display of the time chart 30 when the operator presses the presat button 21, the operator can easily confirm visually a change in a pulse sequence, a process of reduction in the number of slices, and an application frequency of presaturation pulses, when application of a presaturation pulse is added.

Moreover, when the operator presses the interleave button 22 on the scanning-condition edit screen 20 via the input unit 16, the scanning-condition edit/scan positioning unit 17a causes the slice collection order during a repetition time to be reordered by controlling the scanning-parameter limit calculating unit 17b, and then changes display of the time chart 30 based on a result of the reordering.

Figure 5A:
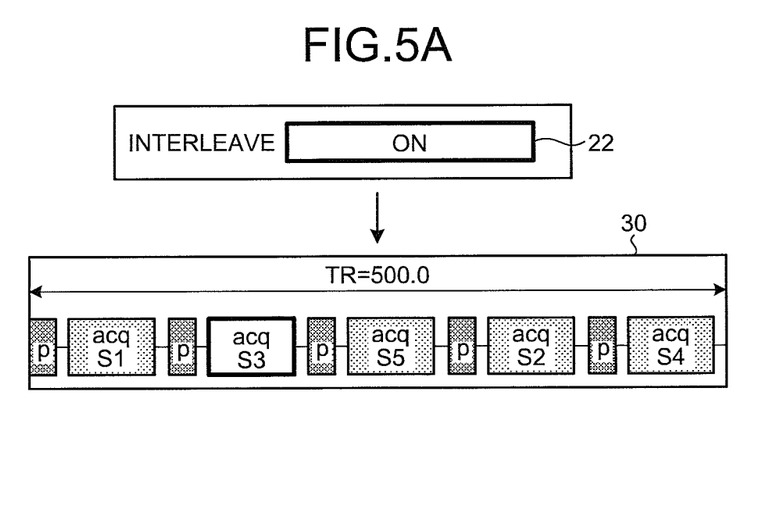
FIGS. 5A and 5B are schematic diagrams for explaining display of the time chart when an interleave button is pressed.
Figure 5B:
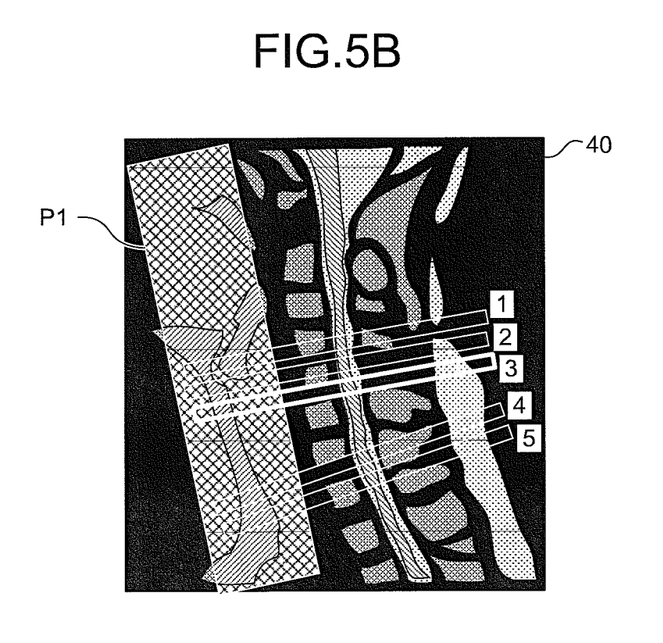

FIGS. 5A and 5B are schematic diagrams for explaining display of the time chart 30 when the interleave button 22 is pressed. As shown in the upper part of FIG. 5A, when the interleave button 22 is pressed, the scanning-condition edit/scan positioning unit 17a reorders the slice collection order displayed on the time chart 30 to the order of "S1", "S3", "S5", "S2", and "S4", from the order of "S1", "S2", "S3", "S4", and "S5".

Conventionally, a change in the slice collection order due to a change in scanning parameters cannot be easily confirmed. However, according to the embodiment, as shown in FIG. 5A, it is clearly stated on the time chart 30 that the order of slice excitation is changed to collect even-numbered slices after collecting odd-numbered slices first, so that the operator can easily confirm a change in the slice collection order by comparing the time chart 30 with that in the previous state shown in the lower part of FIG. 4.

Furthermore, according to the embodiment, the scanning-condition edit/scan positioning unit 17a is configured to synchronize display onto a positioning image performed by the positioning display unit 15b and display of the scanning-condition edit screen 20 and the time chart 30, event by event, thereby more clearly notifying the operator of influence on an image due to a change in scanning conditions.

For example, FIG. 5B depicts an example that scan positions of the following lateral cross sections are planned on a positioning image 40 that is a sagittal section of the neck. According to FIG. 5B, squares numbered "1" to "5" indicate respective slice (slice region) positions. Slice 1 shown in FIG. 5B corresponds to slice S1 on the time chart 30 shown in the lower part of FIG. 5A, and similarly, slice 2 shown in FIG. 5B corresponds to slice S2 on the time chart 30. Similarly, slices 3, 4, and 5 shown in FIG. 5B correspond to slices S3, S4, and S5 on the time chart 30, respectively.

In this way, as the scanning-condition edit/scan positioning unit 17a displays slices on the time chart 30 and slices on the positioning image 40 by associating them in accordance with respective slice numbers, the operator can easily recognize that every other slice is excited from the head side of a subject, subsequently, each slice in-between is excited. In other words, when there is interference between slices due to divergence from an optimal slice property, the operator can easily recognize that the order of excitation is changed to reduce the interference.

Moreover, as shown in FIG. 5B, the scanning-condition edit/scan positioning unit 17a displays a figure P1 that indicates a position of a presaturation pulse on the positioning image 40. Accordingly, the operator can easily grasp a portion to be excited before obtaining each slice data.

Additionally, when the operator specifies, for example, slice 3, on the positioning image 40 via the input unit 16; the scanning-condition edit/scan positioning unit 17a highlights slice S3 on the time chart 30 corresponding to slice 3. On the other hand, for example, when the operator specifies slice S3 on the time chart 30 on the contrary, the scanning-condition edit/scan positioning unit 17a highlights slice 3 on the positioning image 40 corresponding slice S3.

In this way, as the scanning-condition edit/scan positioning unit 17a changes display of a slice on the time chart 30 or the positioning image 40 so as to indicate association between a slice on the time chart 30 and a slice on the positioning image 40, thereby presenting spatial arrangement and temporal arrangement of data collection in an associated manner to the operator.

Returning to FIG. 2, the scanning-parameter limit calculating unit 17b calculates a limit value of a scanning parameter, and creates examination information that indicates scanning conditions for collection of magnetic-resonance signal data. Specifically, upon receiving a value of a scanning parameter from the scanning-condition edit/scan positioning unit 17a, the scanning-parameter limit calculating unit 17b calculates a limit value of another scanning parameter that depends on the received scanning parameter.

The scanning-parameter limit calculating unit 17b then returns the calculated limit value of the scanning parameter to the scanning-condition edit/scan positioning unit 17a, creates each time the examination information 14a indicating scanning conditions for collection of magnetic-resonance signal data based on the received value of the scanning parameter and the calculated value of the scanning parameter, and stores the examination information 14a into the storage unit 14.

The pulse-sequence execution-data creating unit 17c executes a scan by using the examination information 14a stored in the storage unit 14. Specifically, when receiving a start instruction to start a scan from the operator via the input unit 16, the pulse-sequence execution-data creating unit 17c creates pulse-sequence execution data 17d based on scanning conditions stored in the storage unit 14 as the examination information 14a. The pulse-sequence execution-data creating unit 17c then causes the gradient magnetic-field power source 3, the transmitting unit 7, and the receiving unit 9 to execute the scan by sending the pulse-sequence execution data 17d via the interface unit 11.

Figure 6:
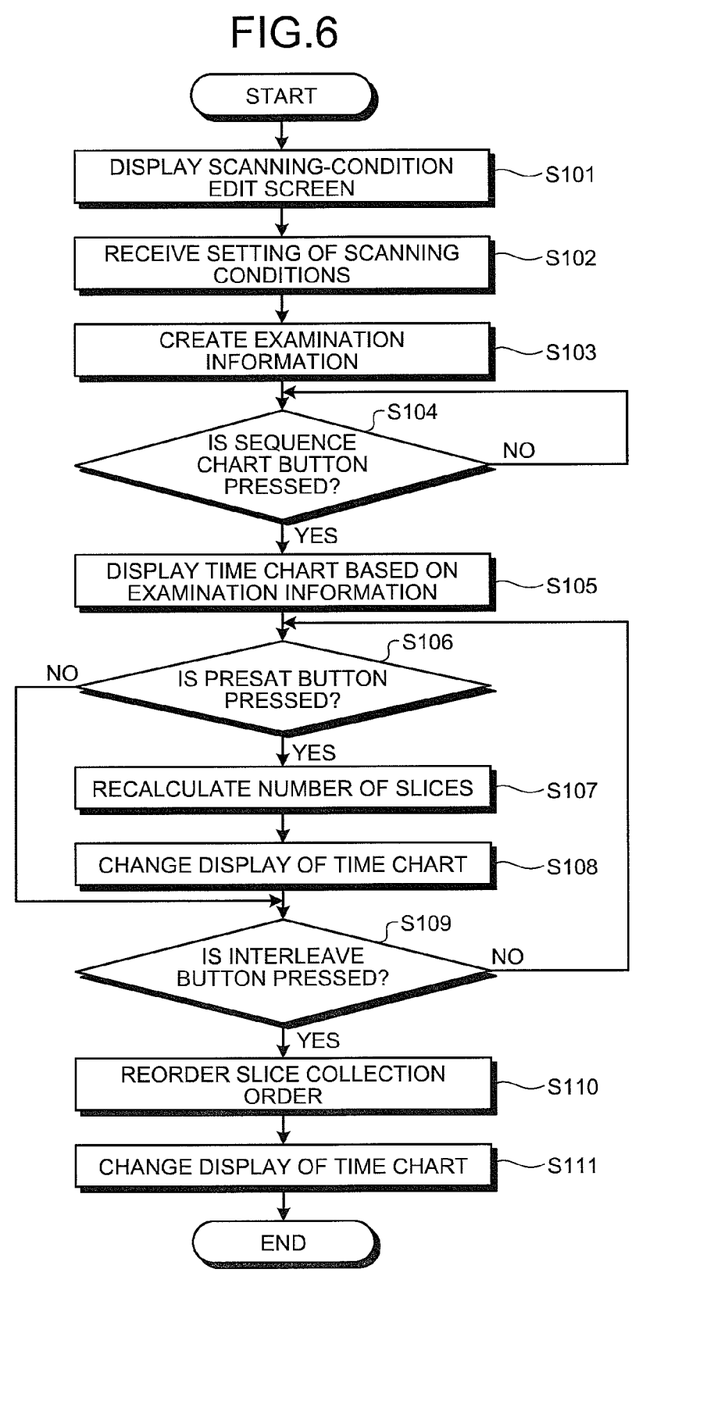
FIG. 6 is a flowchart of a process procedure of time-chart display performed by the MRI apparatus according to the embodiment.

A process procedure of time-chart display performed by the MRI apparatus 100 according to the embodiment is explained below. FIG. 6 is a flowchart of a process procedure of time-chart display performed by the MRI apparatus 100 according to the embodiment.

As shown in FIG. 6, according to the MRI apparatus 100, when receiving a display request to display the scanning-condition edit screen 20 from the operator, the scanning-condition edit/scan positioning unit 17a controls and causes the scanning-condition edit display unit 15a to display the scanning-condition edit screen 20 (Step S101), and receives setting of scanning conditions (Step S102).

When the scanning conditions are then set on the scanning-condition edit screen 20 by the operator, the scanning-parameter limit calculating unit 17b creates the examination information 14a based on the set scanning conditions (Step S103).

After that, if the operator presses the sequence chart button 23 on the scanning-condition edit screen 20 (Yes at Step S104), the scanning-condition edit/scan positioning unit 17a creates the time chart 30 based on the examination information 14a created by the scanning-parameter limit calculating unit 17b, and then controls and causes the time-chart display unit 15c to display the time chart 30 that is created (Step S105).

If the operator presses the presat button 21 on the scanning-condition edit screen 20 (Yes at Step S106), the scanning-parameter limit calculating unit 17b recalculates the number of slices (Step S107), and the scanning-condition edit/scan positioning unit 17a changes display of the time chart 30 based on the recalculated number of slices (Step S108).

If the operator presses the interleave button 22 on the scanning-condition edit screen 20 (Yes at Step S109), the scanning-parameter limit calculating unit 17b reorders the slice collection order (Step S110), and changes display of the time chart 30 based on the reordered slice collection order (Step S111).

As described above, according to the embodiment, the scanning-parameter limit calculating unit 17b creates the examination information 14a that indicates scanning conditions for collection of magnetic-resonance signal data based on a value of a scanning parameter set by the operator; and the scanning-condition edit/scan positioning unit 17a creates the time chart 30 that indicates types and sequential execution-order of events to be executed when collecting magnetic-resonance signal data based on the examination information 14a created by the scanning-parameter limit calculating unit 17b, and causes the time-chart display unit 15c to display the time chart 30. Accordingly, the operator can easily confirm influence on an image due to a change in the scanning parameters.

Although display of the time chart 30 in a case where a two-dimensional spin-echo image is collected according to the multislice method is explained in the above embodiment with reference to FIGS. 3 to 5B, the display style of the time chart 30 is not limited to those shown in FIGS. 3 to 5B, and other display styles appropriate to respective scan types can be used. Respective modifications of the time chart 30 appropriate to other scan types are explained below. The following modifications are explained mainly about processing performed by the scanning-condition edit/scan positioning unit 17a.

(1) Coronary Angiography Combined with Electrocardiogram (ECG) Gating

Display of a time chart for coronary angiography combined with ECG gating is explained below. According to coronary angiography combined with ECG gating, various prepulses are usually applied prior to actual data collection: for example, a prepulse for giving T2 contrast, data collection for compensating motion by detecting body movement, a presaturation pulse for suppressing irrelevant signals outside a region of interest, a pulse for suppressing a fat signal, and a dummy pulse for helping to reach a steady state.

Figure 7:
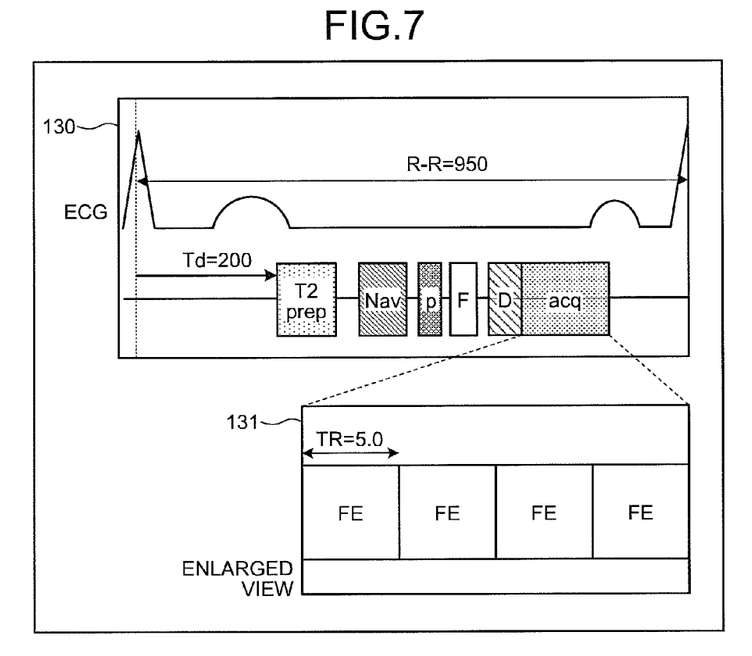
FIG. 7 is a schematic diagram of an example of a time chart according to the embodiment for coronary angiography combined with Electrocardiogram (ECG) gating.

When the examination information 14a read from the storage unit 14 indicates scanning conditions for coronary angiography combined with ECG gating, the scanning-condition edit/scan positioning unit 17a causes the time-chart display unit 15c to display a time chart on which the above prepulses are displayed.

FIG. 7 is a schematic diagram of an example of a time chart for coronary angiography combined with ECG gating. As shown in FIG. 7, for example, the scanning-condition edit/scan positioning unit 17a causes the time-chart display unit 15c to display a time chart 130 on which arranged before "acq" denoting data collection are a figure "T2 prep" denoting a prepulse for giving T2 contrast, a figure "Nav" denoting data collection for compensating motion by detecting body movement, a figure "p" denoting a presaturation pulse for suppressing irrelevant signals outside a region of interest, a figure "F" denoting a pulse for suppressing a fat signal, and a figure "D" denoting a dummy pulse for helping to reach a steady state.

The coronary angiography combined with ECG gating is performed synchronously with an electrocardiographic waveform of a subject, so that each event occurs consistently in accordance with a relative time from an R wave. As shown in FIG. 7, the scanning-condition edit/scan positioning unit 17a conducts display of a simulated electrocardiographic waveform together on the time chart 130, and further conducts display of a time of R-R interval ("R-R=950" shown in FIG. 7) on the simulated electrocardiographic waveform. Moreover, the scanning-condition edit/scan positioning unit 17a conducts display of a delay time from an R wave until a prepulse for giving T2 contrast ("Td=200" shown in FIG. 7).

In this way, as the scanning-condition edit/scan positioning unit 17a conducts display of an electrocardiographic waveform, a time of R-R interval, and a delay time from an R wave as well as the time chart 130, the operator can easily confirm visually a state of producing a pulse sequence that each prepulse is applied for a certain period after 200 milliseconds of a delay time from an R wave, subsequently a dummy pulse is applied, and then data collection is performed during a time phase corresponding to a diastole.

According to the coronary angiography combined with ECG gating, there are several factors relevant to the image quality: for example, data collection is to be performed during a diastole in which cardiac motion is relatively inactive; a data collection time within one heart beat should be set as short as possible within an allowable range in the total scanning time; and a fat suppression pulse "F" and data collection "Nav" for detecting motion are to be executed with timing closely to data collection "acq" as much as possible.

Conventionally, it is difficult for an operator to understand whether scanning parameters of the factors are appropriately set only based on a scanning-condition setting screen. However, according to the embodiment, an electrocardiographic waveform, a time of R-R interval, and a delay time from an R wave until a prepulse for giving T2 contrast are displayed as well as the time chart 130, accordingly, the operator can easily determine whether scanning parameters are appropriately set.

Furthermore, the scanning-condition edit/scan positioning unit 17a can be configured to display a part specified by the operator on the time chart 130 in an enlarged manner in detail. A chart enlarged view 131 shown in FIG. 7 depicts an enlarged view of the data collection part "acq", and indicates that "acq" includes collection of four continuous field echoes.

Usually, more detailed information about a pulse sequence than the chart enlarged view 131 shown in FIG. 7 is not necessarily required for operation of setting scanning conditions. However, the scanning-condition edit/scan positioning unit 17a can be configured to conduct further enlarged display of the chart enlarged view 131 in more detail (displaying a pulse sequence type by type of a pulse, for example, a radio-frequency pulse, a slice-selective gradient magnetic-field pulse, a phase-encoding gradient magnetic-field pulse, and a frequency-encoding gradient magnetic-field pulse). In such case, the scanning-condition edit/scan positioning unit 17a controls to what extent detailed information is to be disclosed, for example, depending on a qualification of an operator.

(2) Imaging by Segmented Field Echo Method

Display of a time chart for imaging by segmented field echo is explained below, according to which a k-space is divided into a plurality of units called segment, and application of a prepulse and ECG gating are performed segment by segment.

Figure 8:
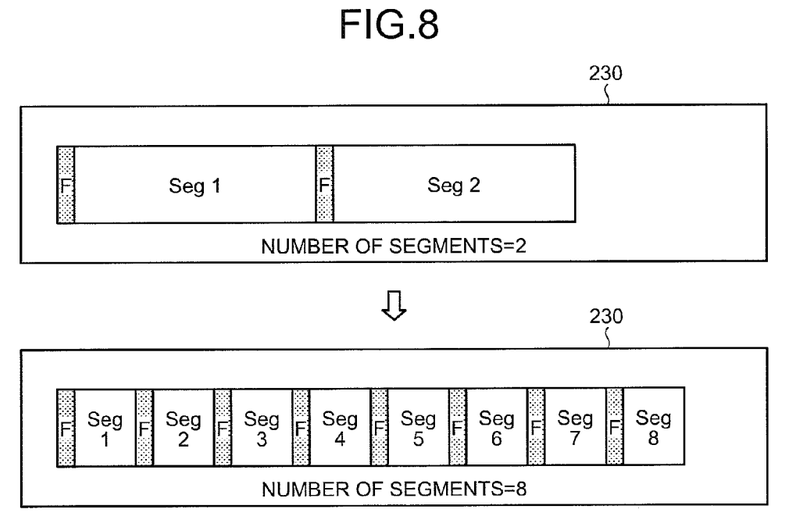
FIG. 8 is a schematic diagram of an example of a time chart according to the embodiment for imaging by a segmented field echo method.

Specifically, when the examination information 14a read from the storage unit 14 indicates scanning conditions for imaging by the segmented field echo, the scanning-condition edit/scan positioning unit 17a causes the time-chart display unit 15c to display a time chart on which figures each indicating a fat suppression prepulse and figures each indicating a segment are alternately arranged.

FIG. 8 is a schematic diagram of an example of a time chart for imaging by the segmented field echo method, and depicts a time chart when fat suppression prepulses are used in combination. As shown in the upper part of FIG. 8, for example, when the number of segments are two, the scanning-condition edit/scan positioning unit 17a conducts display of a time chart 230 on which "F" denoting a fat suppression prepulse, a figure "Seg 1" denoting a first segment, "F" denoting a fat suppression prepulse, and a figure "Seg 2" denoting a second segment are arranged in order.

For example, when the operator changes the number of segments to eight, the scanning-condition edit/scan positioning unit 17a increases figures each denoting a segment to eight as shown in the lower part of FIG. 8, and changes display of the time chart 230 such that each of the fat suppression prepulses "F" is arranged immediately before each of the figures "Seg 1" to "Seg 8" denoting segments.

In this way, as the scanning-condition edit/scan positioning unit 17a changes display of the time chart 230 based on the number of segments set by the operator, the operator can easily confirm that as a result of an increase in the number of fat suppression pulses, a total scanning time is increased even if the other scanning conditions than the number of segments remain the same, and a fat suppression effect is improved because of an increase in the frequency of the fat suppression pulses.

Such influence given to the scanning time and the image quality because of a change in the scanning conditions cannot be explained unless indicating timing of the pulse sequence. Such influence is usually described in an operation manual of a device. However, according to the embodiment, a change in the scanning conditions is displayed simultaneously upon changing a scanning condition when editing the scanning conditions as described above. Accordingly, the operator can understand influence on the image quality more thoroughly.

(3) Angiography by Arterial Spin Labeling (ASL)

Display of a time chart for angiography by ASL is explained below. A method called Time Spatial Labeling Inversion Pulse (Time-SLIP), which is one of ASL methods, is explained below. The Time-SLIP is a method of setting a region of a selective inversion pulse separately from a Field of View (FOV) in order to render a specific blood vessel selectively.

Figure 9A:
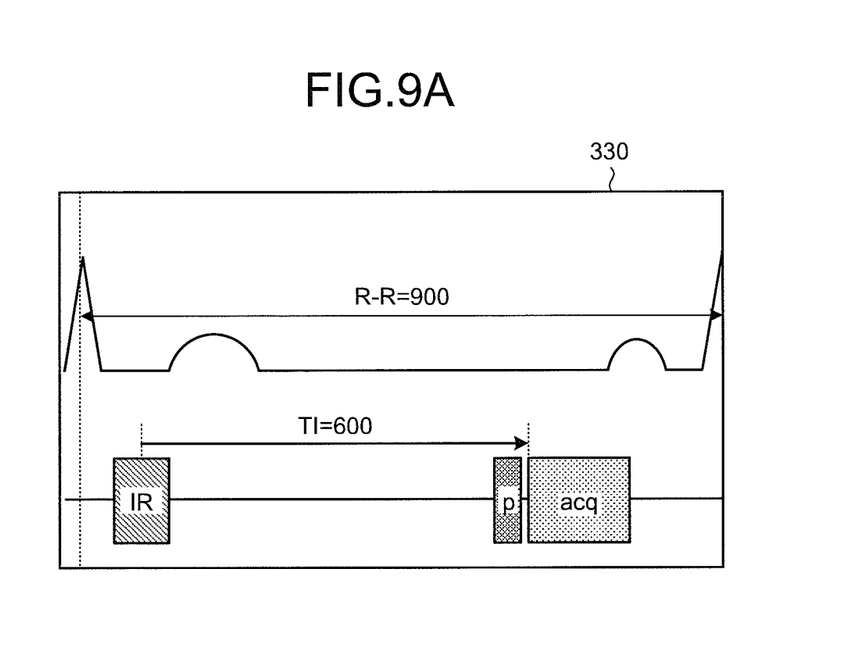
FIGS. 9A and 9B are schematic diagrams of an example of a time chart according to the embodiment for imaging by Time Spatial Labeling Inversion Pulse (Time-SLIP) method.

Specifically, when the examination information 14a read from the storage unit 14 indicates scanning conditions for imaging by Time-SLIP, the scanning-condition edit/scan positioning unit 17a causes the time-chart display unit 15c to display a time chart on which an inversion pulse and data collection are displayed.

Figure 9B:
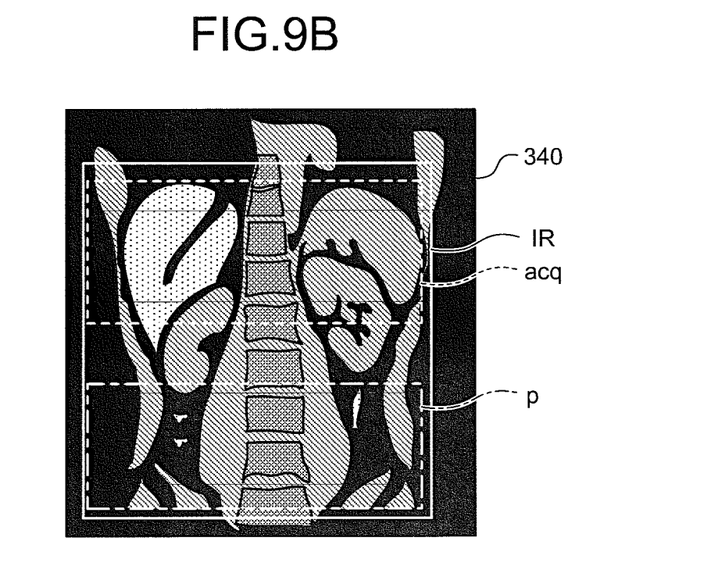

FIGS. 9A and 9B are schematic diagrams of an example of a time chart for imaging by Time-SLIP. FIG. 9A depicts a time chart when rendering only arterial blood flowing into the FOV by collecting data after an inversion pulse is applied and then a certain time elapses. Moreover, according to the example shown in FIG. 9A, a presaturation pulse is applied additionally to another region for suppressing a signal from venous blood flowing in during the same period.

As shown in FIG. 9A, for example, the scanning-condition edit/scan positioning unit 17a conducts display of a time chart 330 on which a figure "IR" denoting an inversion pulse, and a figure "p" denoting a presaturation pulse are arranged before "acq" denoting data collection. Moreover, the scanning-condition edit/scan positioning unit 17a conducts display of a simulated electrocardiographic waveform on the time chart 330 in combination, and further conducts display of a time of R-R interval ("R-R=900" shown in FIG. 9A) and a time from the inversion pulse until the data collection ("TI=600" shown in FIG. 9A) on the simulated electrocardiographic waveform.

When rendering a specific blood vessel by ASL, scanning conditions need to be appropriately set by totally considering running and an approximate blood-flow velocity of the blood vessel, and timing and position of each pulse. According to the embodiment, an electrocardiographic waveform, a time of R-R interval, and a time from an inversion pulse until data collection are displayed as well as the time chart 330, accordingly, the operator can easily determine whether scanning parameters are appropriately set.

When conducting display of the figure "IR" denoting an inversion pulse, the figure "p" denoting a presaturation pulse, and the figure "acq" denoting data collection on the time chart 330, the scanning-condition edit/scan positioning unit 17a can be configured to conduct display of figures in colors, tones, or patterns, such as crosshatching, different from type to type of pulses. The scanning-condition edit/scan positioning unit 17a can then conduct display of figures (rectangles in this case) on a positioning image 340 in the same color, or the same tone, or the same pattern, as that denoting each pulse as shown in FIG. 9B (according to an example shown in FIG. 9B, types of lines of rectangles are varied instead of varying colors, tones, or patterns). Accordingly, the operator can easily understand association between spatial position and temporal order of each pulse.

(4) Display of Position in K-Space of Collected Data

Influences given onto an image that an MRI apparatus obtains by performing Fourier transformation on collected data vary depending on a position of the collected data in an actual space (called k-space). Specifically, it is well known that a signal arranged in the vicinity of the center of a k-space, i.e., a low-frequency region gives influence on the contrast of an image, and contours of the image are influenced by signals arranged in an outer side of the k-space, i.e., a radio-frequency region.

Therefore, the order of collecting data arranged on a k-space is sometimes highly relevant for imaging by an MRI apparatus in some cases. For this reason, the scanning-condition edit/scan positioning unit 17a can be configured to cause the time-chart display unit 15c to display a position of collected data in a k-space together with a time chart.

Figure 10A:
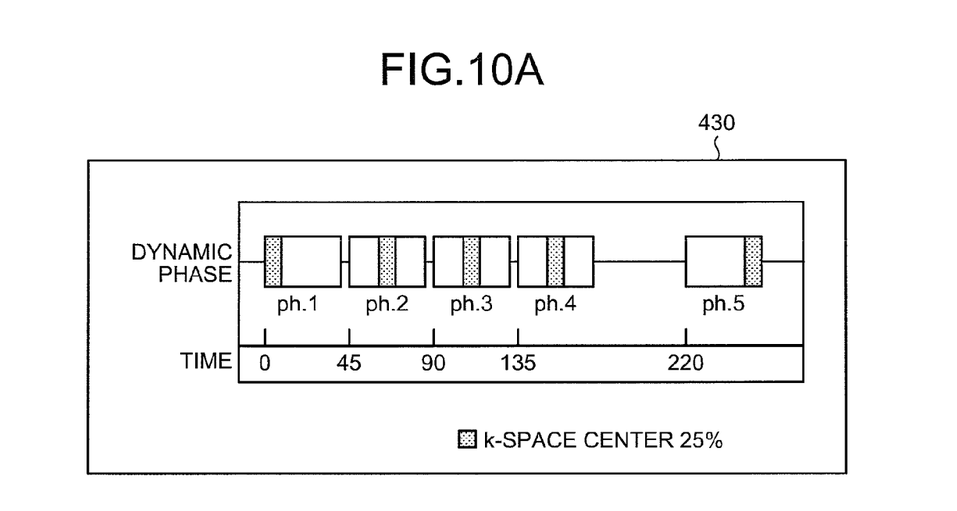
FIGS. 10A, 10B, and 10C are schematic diagrams of an example of a time chart when displaying the position of collected data in a k-space.
Figure 10B:
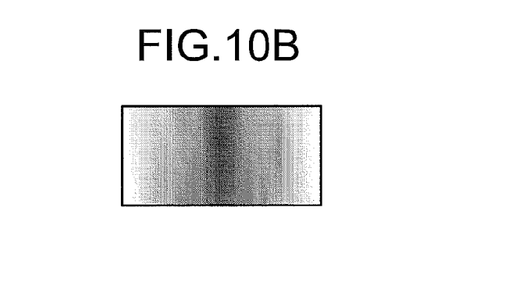
Figure 10C:
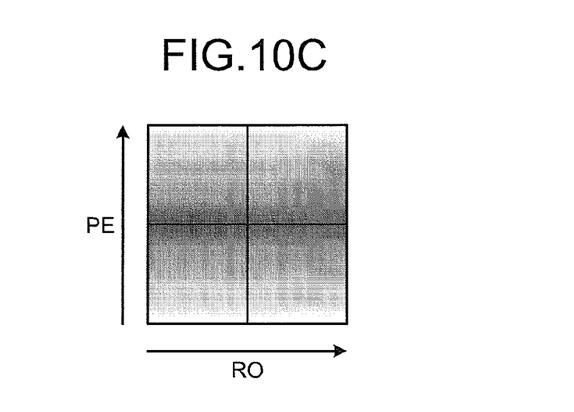

FIGS. 10A, 10B, and 10C are schematic diagrams of an example of a time chart when displaying the position of collected data in a k-space. FIG. 10A depicts an example of a time chart for a so-called dynamic scan, according to which scans are continuously repeated after a contrast agent is injected from a vein.

Specifically, when the examination information 14a read from the storage unit 14 indicates scanning conditions for a dynamic scan, the scanning-condition edit/scan positioning unit 17a causes the time-chart display unit 15c to display a time chart indicating time points of execution timing of continuous scans, i.e., data collection.

For example, as shown in FIG. 10A, the scanning-condition edit/scan positioning unit 17a conducts display of a time chart 430 on which figures "ph. 1" to "ph. 5" denoting the width of data collection in five time phases are arranged together with time points of starting data collection. When displaying "ph. 1" to "ph. 5", the scanning-condition edit/scan positioning unit 17a conducts display of parts denoting collection of data included in a predetermined proportion (for example, 25%) from the center of the k-space, in a color, or a tone, or a pattern different from the other parts.

The contrast of an image obtained through Fourier transformation is determined in accordance with timing of collecting data in the center of the k-space. Therefore, recognition of a time point of collecting data in the center of the k-space from the start of the injection of a contrast agent is highly relevant similarly to recognition of a time point of whole data collection in each time phase, in order to obtain an image with an appropriate contrast.

According to the embodiment, because "ph. 1" to "ph. 5" each denoting the width of data collection are displayed every time phases in a dynamic scan together the time, and the position of collected data in the k-space is indicated to each of "ph. 1" to "ph. 5". Accordingly, it can be easily confirmed whether scanning conditions required to obtain an image with an appropriate contrast are correctly set.

Although FIG. 10A depicts an example of displaying collected data divided into two, namely, a region within 25% from the k-space center, and the other region, the number of regions to be divided are not limited to two, and a region can be divided into more. In such case, display of a figure denoting the width of data collection turns to more detailed one, for example, as shown in FIG. 10B. FIG. 10C depicts the position of collected data in the k-space indicated by the figure shown in FIG. 10B.

Although explained in the above embodiments is a case where a time chart is displayed in an edit process of scanning conditions, the present invention is not limited to this. For example, according to an implementation of the apparatus, if examination information is renewed when creating pulse-sequence execution data, it can be configured such that a time chart can be displayed after the pulse-sequence execution data is created.

As described above, the magnetic resonance imaging apparatus and the scanning-condition setting method according to the embodiments of the present invention are useful for confirming influence on an image due to a change in scanning conditions, and particularly suitable when confirming a sequential order of events to be executed when collecting data.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging apparatus comprising:
a screen display-control unit that causes a display unit to display a scanning-condition edit screen for setting a value of a scanning parameter and to display the value of the scanning parameter on the scanning-condition edit screen;
a scanning-condition setting unit that sets a scanning condition for collection of data indicating an inside of a subject, based on the value of a scanning parameter set by an operator;
a pulse-sequence creating unit that creates a pulse sequence defined by the scanning condition;
a chart display-control unit that creates and causes a display unit to display a time chart of an event related to the pulse sequence;
a data collecting unit that collects data indicating the inside of the subject by executing the pulse sequence; and
an image reconstructing unit that reconstructs an image from the data collected by the data collecting unit, wherein,
when the operator changes the value of the scanning parameter on the scanning-condition edit screen to generate a changed value, the chart display-control unit updates display of the time chart based on the changed value.

2. The apparatus according to claim 1, wherein the chart display-control unit changes further causes the display unit to display on a positioning image, at least one of a position of a slice region and a position of a pulse application region related to the event.

3. The apparatus according to claim 2, wherein the chart display-control unit conducts display of the time chart so as to indicate a time interval with which the event is to be executed.

4. The apparatus according to claim 3, wherein the chart display-control unit controls display of any one of the slice region and the pulse application region on the positioning image and display of the event on the time chart, in conjunction with respect to for each event.

5. The apparatus according to claim 2, wherein the chart display-control unit controls display of any one of the slice region and the pulse application region on the positioning image and display of the event on the time chart, in conjunction with respect to for each event.

6. The apparatus according to claim 2, wherein the chart display-control unit changes any one of a color, a tone, and a pattern of display of an event on the time chart in accordance with a type of the event.

7. The apparatus according to claim 1, wherein the chart display-control unit conducts display of the time chart so as to indicate a time interval with which the event is to be executed.

8. The apparatus according to claim 1, wherein the chart display-control unit changes any one of a color, a tone, and a pattern of display of an event on the time chart in accordance with a type of the event.

9. The apparatus according to claim 1, wherein the chart display-control unit conducts display of the time chart so as to indicate a timing of application of a prepulse and a timing of the collection of data, respectively.

10. The apparatus according to claim 9, wherein when a plurality of prepulses is applied during performing the collection of data, the chart display-control unit conducts display of the time chart so as to indicate an order of application of the prepulses.

11. The apparatus according to claim 9, wherein the chart display-control unit conducts display of the time chart so as to indicate a frequency of application of the prepulse.

12. The apparatus according to claim 1, wherein the chart display-control unit conducts display of information indicating a position of collected data in a k-space together with display of the time chart.

13. The apparatus according to claim 1, wherein the chart display-control unit changes a display style of the time chart in accordance with a type of a scan.

14. The apparatus according to claim 1, wherein the chart display-control unit conducts display of information that is needed for determining whether the scanning parameter is appropriately set, together with display of the time chart.

15. The apparatus according to claim 14, wherein when the examination information represents scanning conditions for coronary angiography combined with Electrocardiogram (ECG) gating, the chart display-control unit conducts display of an electrocardiographic waveform together with display of the time chart.

16. The apparatus according to claim 15, wherein when the examination information represents scanning conditions for coronary angiography combined with Electrocardiogram (ECG) gating, the chart display-control unit further conducts display of a time of R-R interval.

17. The apparatus according to claim 15, wherein when the examination information represents scanning conditions for coronary angiography combined with Electrocardiogram (ECG) gating, the chart display-control unit further conducts display of a delay time from an R wave.

18. The apparatus according to claim 14, wherein when the examination information represents scanning conditions for a scan including application of an inversion pulse and data collection as the event, the chart display-control unit conducts display of a time from the application of the inversion pulse until the data collection together with display of the time chart.

19. The apparatus according to claim 14, wherein when the examination information represents scanning conditions for a dynamic scan according to which a plurality of scans is continuously repeated, the chart display-control unit conducts display of a time point indicating timing of execution of each scan together with display of the time chart.

20. A scanning-condition setting method of a magnetic resonance imaging apparatus, comprising:
  causing a display unit to display a scanning-condition edit screen for setting a value of a scanning parameter and to display the value of the scanning parameter on the scanning-condition edit screen;
  setting a scanning condition for collection of data indicating an inside of a subject based on the value of a scanning parameter set by an operator;
  creating a pulse sequence defined by the scanning condition;
  creating and causing a display unit to display a time chart of an event related to the pulse sequence; and,
  updating, when the operator changes the value of the scanning parameter on the scanning-condition edit screen to generate a changed value, display of the time chart based on the changed value.

\* \* \* \* \*